United States Patent [19]
Rubins

[11] Patent Number: 5,409,445
[45] Date of Patent: * Apr. 25, 1995

[54] BRAIN WAVE SYNCHRONIZER

[76] Inventor: Tye Rubins, 2073 Sunset Plaza Dr., Los Angeles, Calif. 90069

[*] Notice: The portion of the term of this patent subsequent to Apr. 26, 2011 has been disclaimed.

[21] Appl. No.: 164,001

[22] Filed: Dec. 8, 1993

Related U.S. Application Data

[63] Continuation-in-part of Ser. No. 878,825, May 5, 1992, Pat. No. 5,306,228.

[51] Int. Cl.⁶ ............................................ A61M 21/00
[52] U.S. Cl. ....................................................... 600/27
[58] Field of Search ................................... 600/26–28; 128/731, 732, 905

[56] References Cited

U.S. PATENT DOCUMENTS

| | | |
|---|---|---|
| 3,882,850 | 5/1975 | Bailin et al. . |
| 4,008,714 | 2/1977 | Silva et al. . |
| 4,315,502 | 2/1982 | Gorges . |
| 4,335,710 | 6/1982 | Williamson . |
| 4,396,259 | 8/1983 | Miller . |
| 4,456,347 | 6/1984 | Stahly . |
| 4,632,126 | 12/1986 | Aguilar . |
| 4,665,926 | 5/1987 | Leuner et al. . |
| 4,834,701 | 5/1989 | Masaki . |
| 4,902,274 | 2/1990 | Gleeson, III . |
| 4,955,389 | 9/1990 | Schneider . |
| 5,036,858 | 8/1991 | Carter et al. . |
| 5,064,410 | 11/1991 | Frenkel et al. . |
| 5,149,317 | 9/1992 | Robinson ............................. 600/27 |
| 5,306,228 | 4/1994 | Rubins ................................. 600/27 |

FOREIGN PATENT DOCUMENTS 3823402 1/1990 Germany ............................. 600/27

OTHER PUBLICATIONS

"The Science of Light and Sound, " by Theta Technologies, Inc., 1991.
"A Flash in the Brain Pan," by Tom McNichol, in *Health* Magazine, pp. 84–85, Nov. 1991.
"Brain Blasters," column in *Success* Magazine, p. 28, Oct. 1991.
Advertisement for Voyager ® Light/Sound Generator (undated).
Advertisement for Innerquest ® Brain Wave Synchronizer (undated).
Advertisement for Zygon SuperMind TM "Brainwave Entrainment Computer" (undated).
Advertisement for "Relaxation Dream Medium" system by MasterMind.
"Brain Cocktails," Peter Occhiogrosso, Article in *Forbes*, pp. 103–107 (undated).
"Altered States," Article in *Eastsideweek*, Nov. 6, 1991.
"Light & Sound: The Beat of an Ancient Drum," Article in *The New Times*, Mar. 2, 1992.

*Primary Examiner*—Kyle L. Howell
*Assistant Examiner*—John Lacyk
*Attorney, Agent, or Firm*—Poms, Smith, Lande & Rose

[57] ABSTRACT

A device for inducing the brain waves of a user to assume a predetermined frequency comprising a playback device, stereo earphones, and at least one light mounted on glasses in front of each eye of the user. Three separate control signals are pre-recorded superimposed onto a single control track. This composite signal is read by the playback device and is decomposed into the separate control signals by filters in a decoder/controller. One control signal drives a first LED and another drives a second LED. The number of sinusoids within the first and second control signal determine the light intensity. The third control signal is passed alternately to two speakers, with the switching between the speakers being controlled by the state of the first and second control signal. Conventional earphones and a conventional tape player may be used. The invention may be used to selectively activate the pins of a parallel port on a personal computer, to which are connected the LEDs. Also, the invention may include a mercury tilt switch mounted to the spectacles worn by the user to determine if he is dozing off and transitioning into the Theta brain wave state. The spectacles have optional peep holes in the lenses.

15 Claims, 3 Drawing Sheets

BRAIN WAVE SYNCHRONIZER

This is a continuation-in-part of application Ser. No. 07/878,825, filed May 5, 1992, now U.S. Pat. No. 5,306,228.

BACKGROUND OF THE INVENTION

1. Field of the Invention

The present invention relates to an apparatus for inducing desired brain wave frequencies in a user by presenting periodic visual and audio signals to the eyes and ears of the user, respectively.

2. Description of Related Art

It is well known that the human brain generates periodic electrical signals, commonly referred to as "brain waves." These brain waves range in frequency from about 1 Hz to about 36 Hz and, for ease of reference, are commonly divided into four or more groups. "Beta" waves (12 to 36 Hz) tend to dominate in the brain during normal waking activity; "Alpha" waves (8 to 12 Hz) have been discovered to occur most frequently when the person is relaxed; "Theta" waves (4 to 7 Hz) are most common during periods of sleep or deep meditation and also occur during periods of learning or memory recall; and "Delta" waves (1 to 4 Hz) appear most frequently during periods of the deepest sleep. These ranges of frequencies are approximate, but in general, the dominate brain wave frequency increases with increasing mental activity.

Experiments have indicated that when light is repeatedly flashed into the eyes of a subject within this frequency band, the brain waves of the subject tend to assume the frequency of the flashing light. It has also been discovered that such "synchronization" of brain waves may lead to brain seizures in epileptics or in other people who have a history of brain seizures.

On the other hand, experiments have demonstrated that pulsating light and sound can induce a synchronized pattern of brain waves. There is, furthermore, evidence to indicate that by inducing a subject's brain waves to come within the Alpha range, the subject at least will be able to relax better, and may even be able to learn more quickly and permanently. Many researchers also report that a subject whose brain waves are caused to synchronize within the Alpha range or lower are better able to receive subliminal or audible audio messages.

Differential audio frequencies have also been shown to cause similar effects. For example, if the frequency of a tone played into one ear of a subject is 10 Hz higher than the frequency of a tone played into the subject's other ear, experimental evidence indicates that the subject's brain acts in a way similar to a "heterodyne," tending to generate brain waves at a frequency approximately equal to the difference in frequency between the two tones. That is, in this case, 10 Hz. The same result arises when tones are alternately put to the left and right ears with a frequency equal to the desired synchronization frequency.

There are accordingly many devices now available that are designed to present flashing lights, alternating tones, or both, to the eyes and ears of a user. Some devices use "bio-feedback," in which the brain wave frequency of the user is sensed and used to control the frequency of the flashing lights or pulsating tones; the user thereby attempts to train herself to produce the desired frequency, which is reinforced by the flashing lights and pulsating tones. Many other devices, which do not measure the brain waves in an attempt to create a feedback loop, actively control the flashing or switching frequency. Examples of such devices are described in the following U.S. patents:

| U.S. Pat. No. | Inventor(s) | Issue Date |
| --- | --- | --- |
| 5,064,410 | Frenkel, et al. | Nov. 12, 1991 |
| 5,036,858 | Carter, et al. | Aug. 6, 1991 |
| 4,955,389 | Schneider | Sept. 11, 1990 |
| 4,902,274 | Gleeson, III | Feb. 20, 1990 |
| 4,834,701 | Masaki | May 30, 1989 |
| 4,665,926 | Leuner, et al. | May 19, 1987 |
| 4,632,126 | Aguilar | Dec. 30, 1986 |
| 4,456,347 | Stahly | June 26, 1984 |
| 4,396,259 | Miller | Aug. 2, 1983 |
| 4,335,710 | Williamson | June 22, 1982 |
| 4,315,502 | Gorges | Feb. 16, 1982 |
| 4,008,714 | Silva, et al. | Feb. 22, 1977 |
| 3,882,850 | Ballin, et al. | June 13, 1975 |

All of these known devices create the synchronizing pulsed light and/or sound by actively generating an electrical pulse at the desired frequency. This electrical synchronization pulse activates a small set of lights in front of the user's eyes, and controls a tone generator whose signal is fed into earphones. In many of these conventional devices, the electrical pulses result from a timing program in the memory of a microprocessor or a computer. In some of these devices, the user herself selects the synchronization frequency. In other devices, one or more frequencies or programs of varying frequency are generated automatically, whereby the user, in some cases, can select which program she wishes to follow.

The foremost drawbacks of known devices for synchronizing brain waves are that they are complicated and expensive. They typically contain many mechanical and electrical components that require careful testing and calibration. Few are suitable for easy use by most individuals, and fewer still are within their budgets. Even the least expensive of these known devices sells at retail for prices on the order of hundreds of dollars.

In order to reduce complexity, at least one device (see the patent to Gleeson) encodes control signals on magnetic tape. Such devices, however, typically require four or more audio channels simultaneously, so that they are not suitable for use in common 2-channel devices such as the portable stereo cassette tape players already owned by a large section of the population. Furthermore, the Gleeson device requires special conditioning circuitry separate from the tape player in order to drive the lights and speakers used; this increases design costs.

It is therefore an object of this invention to provide a device for inducing synchronized brain waves using both flashing lights and pulsating tones that is easy to use and that can be manufactured from inexpensive and compact components so as to make it much more affordable than existing devices. It is another object to adapt the present invention to a personal computer. It is yet another object of the present invention to detect when a user enters the Delta brain wave state.

SUMMARY OF THE INVENTION

The present invention relates to a playback device, stereo earphones, and at least one light mounted on glasses in front of each eye of the user. In an exemplary embodiment, first, second and third control signals are prerecorded superimposed onto a single control track. The playback device, which may be a conventional tape player, reads the control track, and the corresponding electrical composite signal is transmitted via standard connectors to a decoder/controller. The decoder/controller includes one filter (preferably band-pass) for each of the three control signals.

The first control signal, after filtering and extraction from the composite signal goes to an operational amplifier (Op Amp), the construction of which is well known within the art. The Op Amp drives a light. The second control signal drives a second light in a similar manner. The intensity of illumination of the lights is controlled by varying the number of sinusoids in the respective control signal.

The first and second control signals are recorded as "bursts", with a non-zero frequency during active period portions and an amplitude of substantially zero during inactive period portions. The state of each signal controls the states of speaker switches that alternately pass the third control signal to left and right speakers or to both speakers depending on the state of the respective signal. Conventional earphones and a conventional tape player may be used. The invention also includes the method according to which the control signals are prerecorded, played back, filtered, and applied to the lights and speakers.

In an alternative embodiment, the present invention is incorporated into an IBM personal computer, or any similar computing device. A program, stored on a hard drive, floppy disk, CD-ROM, or other media is loaded into the PC's RAM. The operating program contains brain synchronization data and an audio program. Executing the operating program outputs the synchronization program signal and audio program signal through an interface port. In an exemplary embodiment, parallel port pins of the PC are used to conduct the signals to a headset and spectacles with LEDs as arranged above. Specific pins in the parallel port are actuated and the LED in the spectacles are consequently triggered. Similarly, tones in the headset can be generated by triggering select pins in the parallel port. Of course, other interface ports can be used. Thus, the present invention is easily adaptable to the numerous PCs already in many homes.

In yet another alternative embodiment, the present invention provides a Delta wave sensor, which is a simple motion sensor. When a user enters the Delta wave state, he or she becomes drowsy, a sign that the brain is transitioning into the Delta state. If the user is sitting upright, her head inevitable droops forward. Therefore, when the motion sensor is mounted to the spectacles of the present invention, and the user's head droops forward, the motion sensor detects the change in condition and consequently triggers an audible alarm, and/or changes the frequency of the light pulses. Preferably, the motion sensor is a mercury tilt switch known in the art. Once the head of the user droops forward at a 45 degree angle or more, the mercury switch closes a circuit containing a common tone generator, which produces an audible tone. The tone is useful to keep the user awake and out of the Delta state, wherein the user completely loses consciousness falls asleep.

Alternatively, the motion sensor can trigger a circuit known in the art that increases the frequency of the light emitted from the LED, and/or increases the frequency of the audible tone. The overall effect of the increasing frequency of the tone and light prevents the user from transitioning into the Delta state. Hence, the present invention Delta sensor is a useful bio-feedback device for maintaining the user in the Theta brain wave state.

DETAILED DESCRIPTION OF THE DRAWINGS

Figure 1:
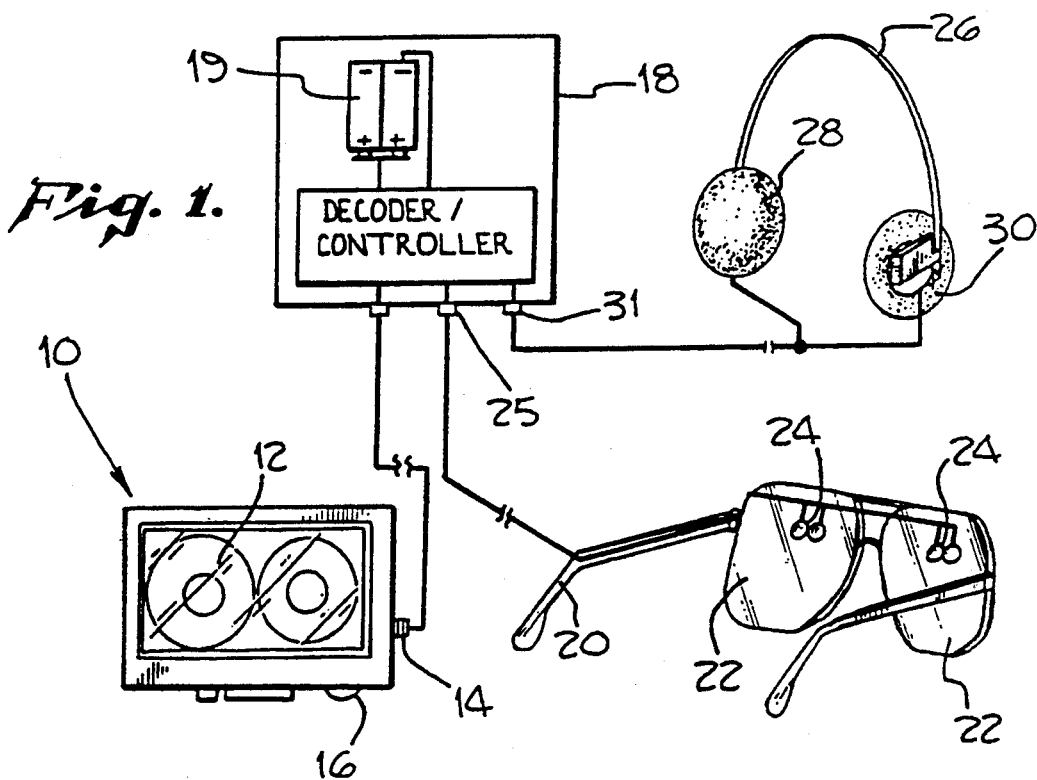
FIG. 1 illustrates the main components and general configuration of the brain wave synchronizer according to the invention.

FIG. 1 shows the main components of the system according to the invention. A standard, commercially available tape player is indicated generally by reference number 10. A standard cassette tape is indicated by reference number 12. The tape player 10 includes a least one audio output 14 and a volume control 16. It is not necessary according to the invention for the tape player 10 to be portable; instead, any tape player may be used, and application of the invention to other technologies such as reel-to-reel tape players, CD players, and digital audio tape players is also possible. The invention requires only that there be some audio output, for example, the output normally used to connect the tape player to headphones.

According to the invention, the recording medium such as the cassette tape 12 needs one track for recording an audio control signal. If the invention is used in combination with another audio program such as a self-help message or other learning program, the recording medium should have at least one other track for carrying this program. The invention is therefore well-suited for use with a standard stereo cassette tape.

The invention also includes a decoder/controller device 18, whose construction and operation are described below. As FIG. 1 illustrates, the user will normally plug the decoder/controller 18 into the output 14 of the tape player 10. The decoder/controller 18 therefore receives the left and right audio tracks of the stereo output. Either of the left or right track can be used as the control track with the unused track being sent directly to the earphones or speakers. After decoding the control signal (described below), the decoder/controller 18 generates signals that control audio and visual synchronization signals. The decoder/controller 18 also houses one or more standard batteries 19 that provide electric current to the circuity of the decoder/controller.

In order to present flashing visual signals to the eyes of the user, the invention includes glasses 20 with opaque lenses 22 and at least one light 23, 24 mounted on each lens in front of the eye of the user. The glasses 20 are preferably inexpensive, standard glasses whose lenses are covered with an opaque material. This material may be such as a metallic foil, but is it preferably a printed circuit board, which not only shields the user's eye from ambient light, but also carries standard etched or attached conductors that lead electrical current to the lights.

The lights 23, 24 are preferably pairs of light-emitting diodes (LEDs). Such LEDs draw little electrical current and have a sufficiently fast on/off response that the user can clearly sense that they are flashing at or below frequencies in the Beta range. The color of the lights 23, 24 is not essential according to the invention as long as the light is visible. It is not necessary to include two paired lights in front of each of the user's eyes. Paired lights are preferred, however, since they provide a wider field of view than a single LED. This in turn makes the glasses 42 more universally useful and reduces the expense of having to manufacture the glasses with different placement of the lights.

One light per eye may, however, be used if it has sufficiently wide field of view and is sufficiently bright. In this context one should also keep in mind that the user's eyes will usually be closed while she is using the invention, and the flashing of the lights must then be visible through her eyelids.

The glasses 20 are connected to the decoder/controller 18 using a standard electrical connector, jack or plug 25. The number of electrical connectors between the decoder/control and the glasses 20, and why, is explained below.

The invention also includes common stereo earphones with a left speaker 28 and a right speaker 30. The earphones 26 are connected to the decoder/controller using a conventional stereo earphone jack 31.

FIG. 1 illustrates one of the main cost-saving advantages of the invention. Most users will already own a tape player 10 and headphones 26 suitable for use with the invention. Even for those users who do not yet own such equipment, the cost of a satisfactory tape player with accompanying headphones, together with the cost of the decoder/controller 18 and glasses 20 according to the invention, will still be much less than the cost of existing devices designed to synchronize brain waves.

According to the invention, control signals for driving the pulsating lights 23, 24 and alternating audio tones in the earphones 26 are pre-recorded using known recording equipment onto a single tract of the cassette tape or other recording medium. The control signals in the preferred embodiment comprise a superimposition of three separate audio frequencies onto the control track. These frequencies, labelled f1, f2, and f3 below, are sufficiently separated in the audio range that corresponding band-pass filters (described below) are able effectively to filter out the other two frequencies while passing its center frequency, which is approximately the frequency of the corresponding control tone.

Signals f1 and f2 are pulsating sine waves. During the recording process, the rate of pulsation is equal to the desired brain wave frequency ("pulse"). Each pulse's beginning and ending is determined by a preprogrammed or manually operated sequencer, the construction of which is well know within the art. Furthermore, the number of sinusoids within each pulse can be changed, during the recording process, to control the intensity of illumination of the lights, as is explained below. Furthermore, since f3, which is also a sine wave, will be used as the audio tone in the earphones 26, f3 should be chosen to be comfortable to listen to; frequencies within one octave on either side of middle C are, for example, suitable.

Figure 2:
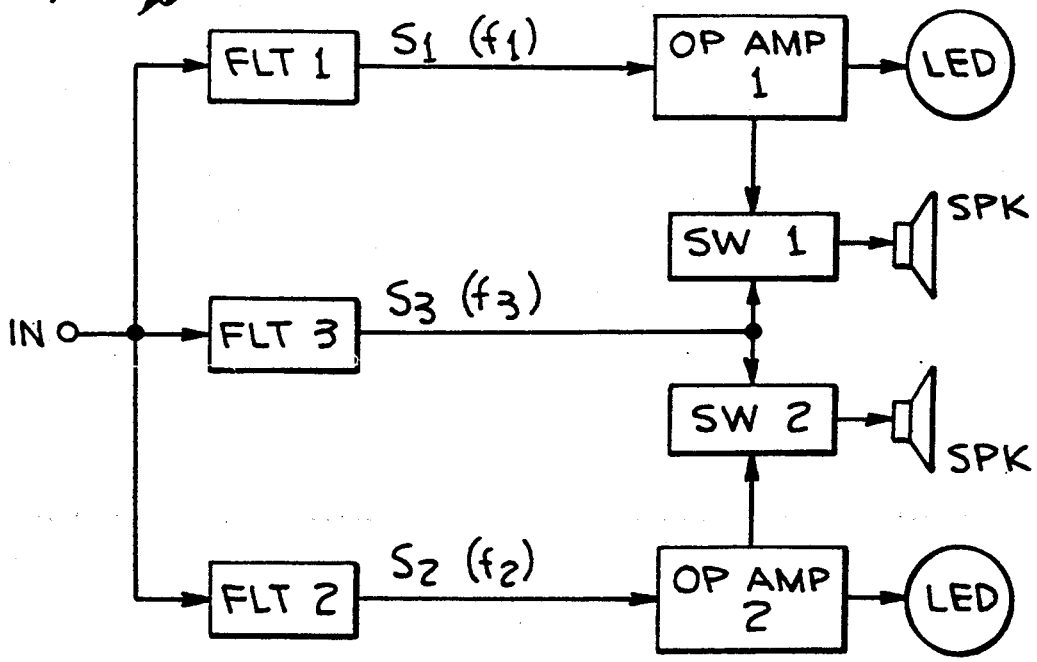
FIG. 2 is a simplified block diagram of the decoding and control circuitry used in the invention.

FIG. 2 is a block diagram that shows the general structure of the circuitry of the decoder/controller 18. The audio input signal from the control track of the cassette tape is indicated at the left as the signal IN. The signal IN first passes to a bank of three filters FLT1, FLT2, and FLT3. The output signals from the filters FLT1, FLT2, and FLT3 are S1, S2, and S3, respectively. The dominant (and for an ideal band-pass filter, the only, frequency of each output signal S1, S2, and S3 , is f1, f2, and f3, respectively. In the preferred embodiment, the filters are band-pass filters, although a low-pass only filter may be used to extract the lowest-frequency control signal from the input signal IN.

Output signals S1 and S2 are both sine waves and are both used in three ways. First, signals S1 and S2 are used to switch on and of LED1 and LED2, respectively. Each signal, S1 or S2, goes to a separate and identical Op Amp. The Op Amp activates a light. Since the frequency of both S1 and S2 is greater than the frequency of the desired brain waves pulse, i.e. greater than 40 Hz and the approximate threshold of human visual perception, the light appears to be on continuously during each pulse.

Second, signals S1 and S2 are used to control the intensity of illumination of the lights. Since the lights are activated, turned on and off, at the same rate as the frequency of the sine waves of S1 and S2, removal of any of the sinusoids from either signal during the recording process will reduce the number of sinusoids going to the respective Op Amp and activating the lights. While the pulse remains unchanged, the reduction in intensity of illumination of the lights during the pulse is directly proportional to the number of sinusoids removed from the signal during the pulse. In other words, this reduces the number of times the lights are activated during the pulse which means the total illumination over the period is reduced.

Figure 4:
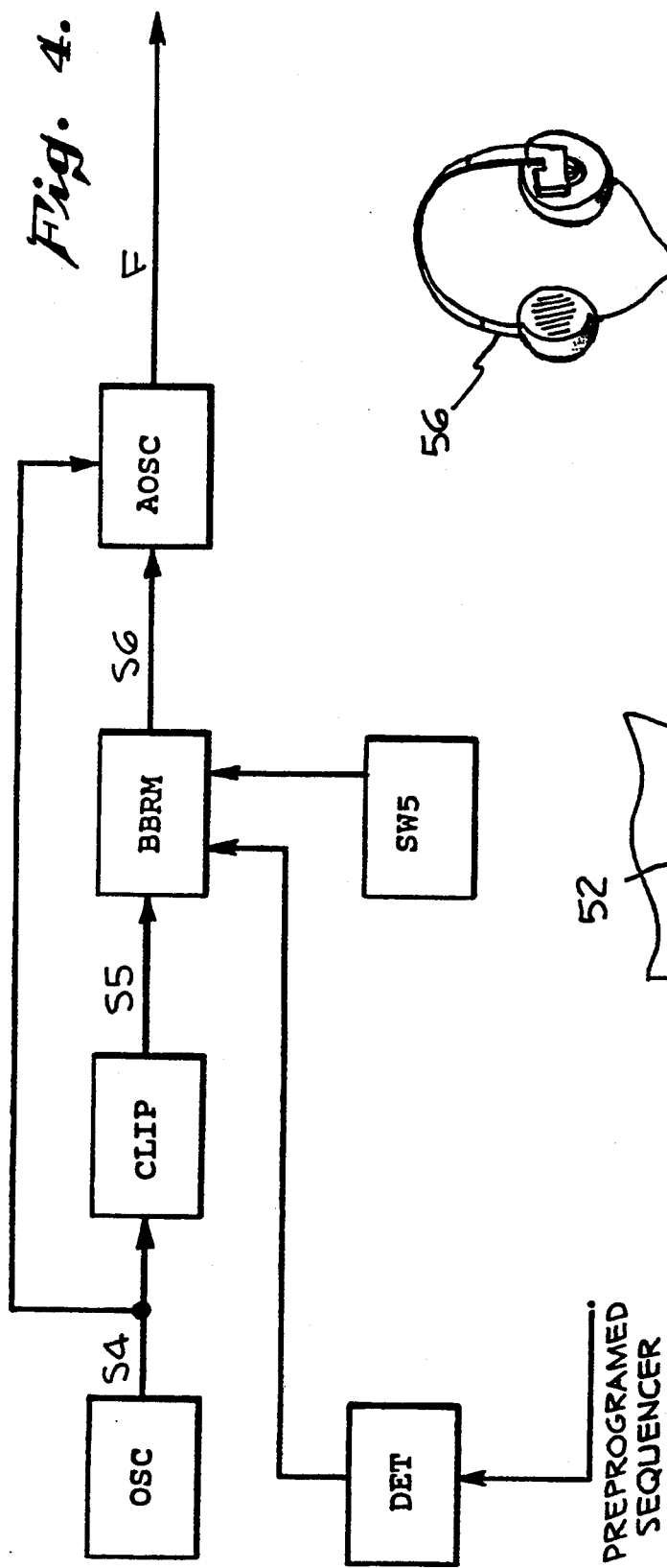
FIG. 4 is a simplified block diagram of the intensity encoding device used in the invention.

One method to accomplish this part of the invention occurs during the recording of F1 and F2 and is illustrated in FIG. 4. Preferably, an oscillator (OSC) generates a continuous sine-wave tone of 2800 Hz (S4); this is an example only and the tone need not be of this frequency. Signal S4 goes through a clipper (CLIP) which shapes the S4 into square waves (S5). Signal S5 is used as a clock for a binary bit-rate multiplier (BBRM). The preprogrammed sequencer activates a detector (DET) which determines the beginning and ending of each pulse. This information goes to the BBRM which pulses signal S6 on and off at the desired brain wave frequency or pulse. A binary switch (SW5) controls the BBRM and determines the number of square waves that will be in each pulse of S6. The signal S6 goes to an analogous sine wave oscillator (AOSC) which produces the signal to be recorded, F (f1 or/and f2). To produce both f1 and f2 with dissimilar or alternating pulsation rates, two such devices as described above would be required. The construction of the above is well-know within the art.

Third, signals S1 and S2 are also used according to the invention to control the switching from one ear to the other of an audio tone into the earphones, (SPK1 and SPK2). This audio tone itself is carried by the third signal S3 and is present at switches SW1 and SW2. The presence of S1 and S2 activates switches SW1 and SW2, respectively. The activation of either SW1 or SW2 passes S3 to SPK1 or SPK2, respectively.

Although not necessary according to the invention, the third signal S3 preferably includes two frequency components that differ in frequency by an amount equal to the desired brain wave frequency. For example, if the base frequency of the audio tone in the earphones is chosen to be 440 Hz (middle A) and the desired brain wave frequency is 10 Hz (in the Alpha range) the second frequency component of S3 would be chosen to be 440 Hz±10 Hz.

As is mentioned above, experimental results indicate that the human brain "cancels out" or "heterodynes" the frequencies and responds as if it were subject to the differential frequency. Since the frequency difference will in all cases be small (less than approximately 36 Hz, since the desired brain wave frequency will normally be in the Beta range or lower), both of these frequencies will normally fall easily within the pass-band of the third filter FLT3. It is not necessary to include two frequency components in the signal S3 if no "heterodyning" effect is sought. Rather, S3 may then be a simple single-frequency audio tone.

Figure 3:
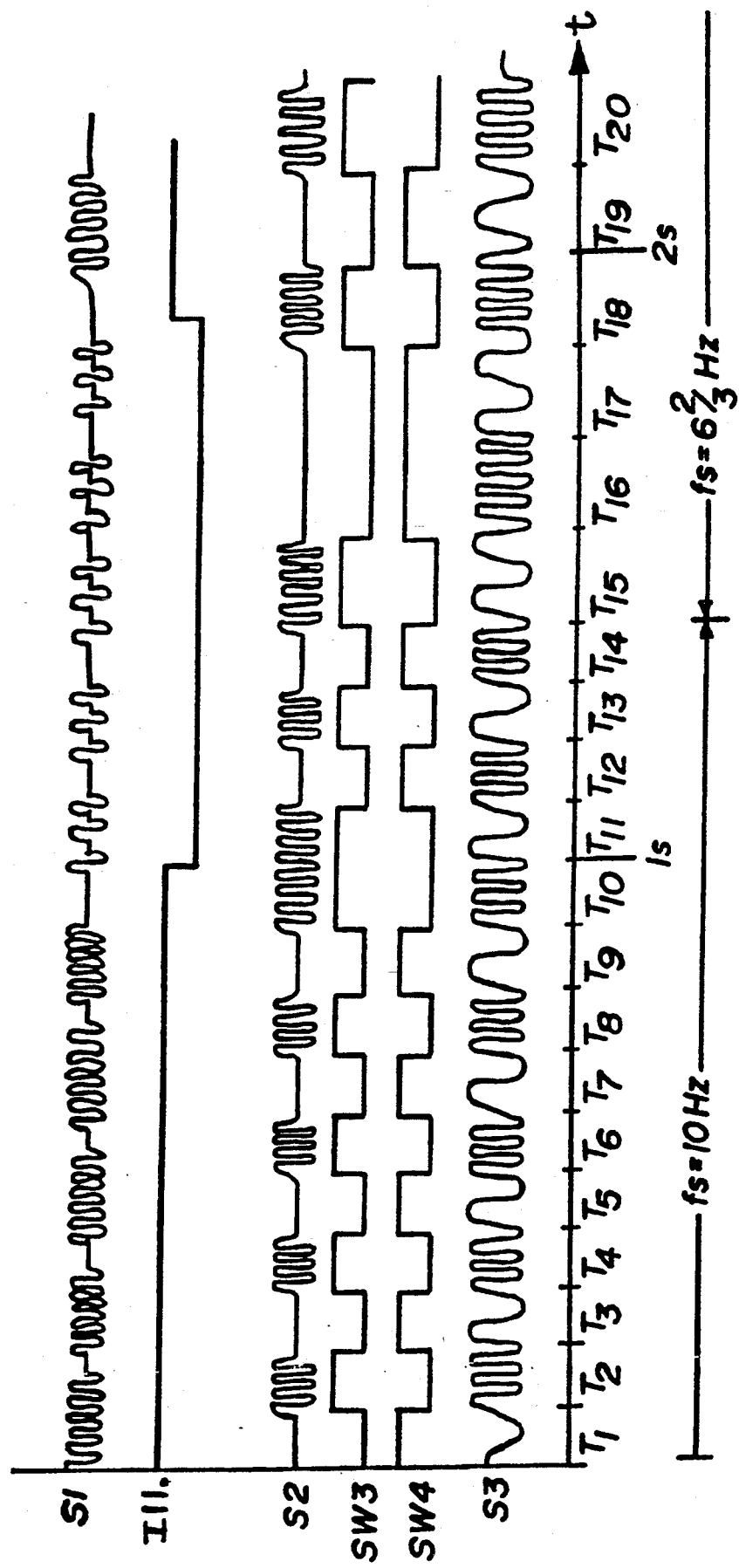
FIG. 3 illustrates graphically a simplified example of the structure and sequencing of a three-tone audio control track used as an input to the decoding and control circuitry.

FIG. 3 illustrates graphically an example of a portion of a time history of various signals in the circuit according to the invention. FIG. 3 does not show precise wave forms or amplitudes, but is rather a simplified, qualitative illustration of the timing and general relationship of the signals. According to the invention, signals S1, S2 and S3 are pre-recorded using known recording equipment onto a single track of the recording medium. Signal S3 is recorded directly. Signals S1 and S2 are processed prior to recording to make the number of sinusoids within each pulse proportional to the percent illumination desired. In FIG. 3, these signals are shown separately, that is, after separate filtering. On the control track of the recording medium, these three signals are superimposed on each other to form a singletrack, multi-control signal.

One significant advantage of this invention is therefore that it is not necessary to provide special signal generators, timing circuitry, or specialized microprocessor programming in any component that the user would have to buy in order to use the invention; instead, all necessary control signals are generated in a recording studio, and can then be put easily on a large number of inexpensive standard cassette tapes. Furthermore, the number of different synchronization routines is not limited to some predetermined and pre-programmed set, but rather may be varied for all users simply by mass recording of a new routine onto cassette tapes that can be made available to all at low cost.

In FIG. 3, the left portion of the horizontal time axis is divided into fourteen 1/10th second intervals T1-T14. Since the period is equal to the inverse of the frequency, the synchronization frequency $f_s$ in these intervals is 10 Hz (in the Alpha range). This is chosen by way of example only. After the fourteen 1/10th second period, it is assumed, also by way of example, that the synchronization frequency $f_s$ is to drop to 6⅔ Hz, corresponding to a signal period of 15/100 seconds. Six such period T15-T20 are illustrated in FIG. 3.

The second signal S2 controls the flashing of the second light LED2. Over the first ten periods T1-T10 S2 is present when S1 is absent. This means that the two lights LED1 and LED2 flash alternately. This is not necessary according to the invention. Rather, during the intervals T11, T13, and T15, S1 and S2 are synchronized, so that the lights will flash simultaneously. Since S1 and S2 are independent of each other, any pattern of flashing can be created simply by recording the two signals S1 and S2 with the desired sequencing.

The signal S3 determines the audio tone that the user will hear in the earphones or speakers SPK1 and SPK2. In the example shown in FIG. 3, the signal S3 alternates between two frequencies. This frequency shift is optional according to the invention, but if it is used, the frequency difference should preferably be equal to the desired synchronization frequency $f_s$. (In FIG. 3, the wave form for signal S3 is illustrated in greatly simplified form for the sake of clarity; for a base tone of 440 Hz, for example, signal S3 will go through 44 full cycles during each interval T1 through T10.) In the example shown in FIG. 3, the signal S3 has its higher frequency during each even-numbered time interval (T2, T4, T6, etc.) and its lower frequency during each odd-number interval. The signal S3 is recorded easily using known signal synthesizers and recording equipment.

During the first ten periods T1-T10 of the example illustrated in FIG. 3, the user will see lights that flash alternately left-right at a frequency of 10 Hz, and will hear a tone that switches back and forth between the left and right ears at a frequency of 10 Hz. Additionally, the tone heard in the one ear will be 10 Hz higher than the tone heard in the other ear.

According to the invention, the intensity of the flashing lights LED1 and LED2 can be controlled and varied according to a predetermined program during the original recording of the control track, for example, on a master tape.

During the time intervals T11-T15, the user will see lights that flash simultaneously in both eyes, with an intensity less than during the preceding ten intervals. The user will still, however, hear alternating tones of a slightly different frequency from ear to ear. During the time intervals T17-T20, the user will once again see alternating flashing lights at the lower intensity, and will hear alternating tones of slightly different frequency but during these intervals the synchronizing frequency will be lower since the "burst" and "pause" periods of the signals S1 and S2 are longer than during the first ten time intervals. Of course, in actual use a given frequency of lights and tones will normally continue for much longer than is illustrated in FIG. 3, but they do not necessarily have to do so; any pattern is possible by suitable pre-recording of the control signals S1, S2, and S3. As is mentioned above, the frequencies of the control signals S1, S2, and S3 should be separated sufficiently so that each filter FLT1, FLT2, and FLT3 will be able to reject that two control signals other than the control signal at or near its center frequency.

One advantage of the invention is that most of the components in the decoder/controller are readily available in the market and are inexpensive. Furthermore, components such as the active filters are readily available as small, inexpensive, integrated circuits incorporated into single chips. This helps to keep the decoder/controller both small and affordable. No signal generation circuitry is required, since the frequencies and timing of the control signals are arranged in advance during the recording of the control track of the cassette tape.

By centralizing the control function to the original recording studio that makes a master tape, no separate expensive microprocessor-controlled signal generation is required by the user.

Note that the playback speed of standard cassettes, compact discs, etc., is standardized, so that a control or audio signal recorded at, say, 5 Hz will not be "" or "compressed" significantly during playback. Furthermore, the frequency of the "bursts" (typically at the synchronization frequency) will not change substantially if the tape speed is kept within the limits normally found in conventional tape players.

In an alternative embodiment, the present invention is adapted for use with a personal computer or similar device. For the sake of illustration, the following discussion applies the present invention to an IBM compatible computer, but it is clear that the present invention can be used on other computing devices.

In a preferred embodiment, the brain synchronization program and audio program are easily stored in the computer hard drive, floppy, CD-ROM disk, digital tape drive, or like data storage medium. With the user at the keyboard, the brain synchronization program and audio program are called up and executed in the RAM through processes well-known in the art.

Through conventional software commands, various pins in a parallel interface port of the PC are selectively activated. The activated pins in the parallel port in turn are used to actuate the LEDs in a spectacle configured as shown above. Further, selected pins are used to transmit an audible signal to earphones worn by the user. Although a parallel port is used, other interfaces are possible. For example, a game card port, a sound card port, or the like can be used for output of the brain synchronization program data and the audible program to the LEDs and earphones, respectively.

Figure 5:
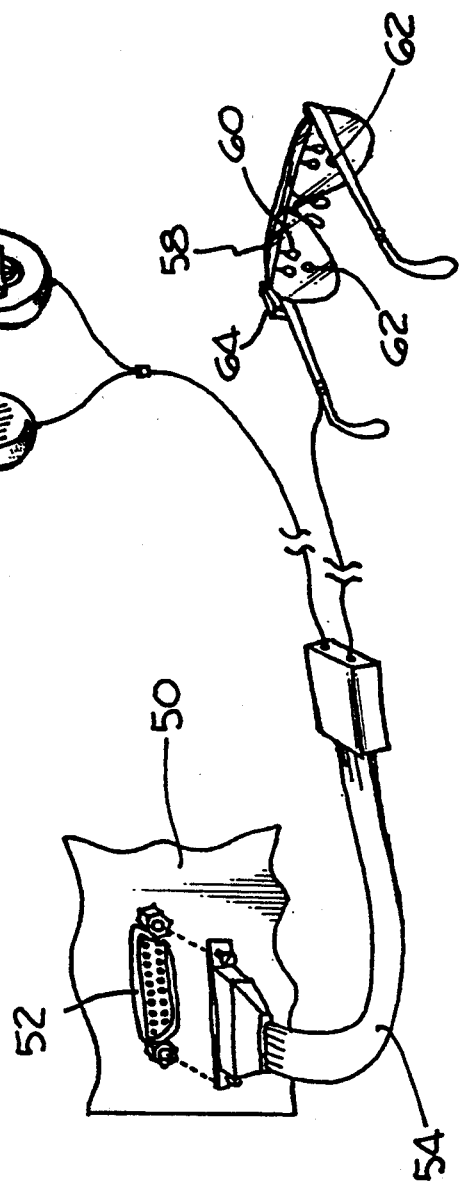
FIG. 5 shows an alternative embodiment of the present invention having a control source originating from a PC via a parallel port, and incorporating a motion sensor in the spectacles.

FIG. 5 shows the above alternative embodiment. The personal computer 50 is shown in a cutaway view, and can be of any configuration known in the art. In the back of the computer 50 is a standard Centronics or like parallel interface port 52, again known in the art. The parallel port 52 can receive or transmit data. TABLE 1 shows the industry standard configuration of the parallel port, as follows:

TABLE 1

| PIN | SIGNAL |
|---|---|
| 1 | −STROBE |
| 2 | DATA0 |
| 3 | DATA1 |
| 4 | DATA2 |
| 5 | DATA3 |
| 6 | DATA4 |
| 7 | DATA5 |
| 8 | DATA6 |
| 9 | DATA7 |
| 10 | −ACK |
| 11 | BUSY |
| 12 | PAPER EMPTY |
| 13 | +SELECT |
| 14 | AUTO FDXT |
| 15 | −ERROR |
| 16 | −INIT |
| 17 | −SLCTIN |
| 18−25 | GROUND |

In a typical computer, DATA pins 2 through 9 each is approximately +5 volts with a limit of 20 mA and are used by one embodiment of the instant invention; however, the present invention is not restricted to pins 2 through 9, nor is it restricted to the parallel port 52. Other user interface ports may be used insofar as data can be readily transferred into and out of the computer.

As mentioned above, very simple software containing the desired brain wave synchronization program and audible program can be written by any qualified computer programmer. The software is stored in a variety of media and executed by the microprocessor in the personal computer through any conventional process. The computer hardware is standard and does not form a part of the present invention; therefore, it is not shown in detail in FIG. 5.

The synchronization program and audible program in the present embodiment contain the same data as in the above embodiment. The data is sent through the DATA pins of the parallel port 52 to cable 54, and suitable divided and channeled to a headset 56 with earphones and to a pair of spectacles 58 configured as before. LEDs 60 mounted on the spectacles 58 are in turn operated by the synchronization program, while the audible program is reproduced in the headset 56. The 5-volt output voltage from the DATA pins are adequate to drive the transducers in the headset 56 as well as triggering the LEDs 60.

The spectacles 58 include optional peep holes 62 allowing the user to look through the spectacles 58 and see images on the computer monitor. This enables coordination between an audio stimulus and a visual stimulus which enhances the performance of the device. For example, when the present invention induces the user into an Alpha brain wave state in which the brain is conditioned for learning, a visual program containing a foreign language lesson can be viewed simultaneously on the monitor.

In yet another alternative embodiment, the present invention provides an optional Delta wave sensor, used to keep the user from falling asleep and transitioning into the Delta wave state. In an exemplary embodiment shown in FIG. 5, the Delta wave sensor is a common motion sensor 64 positioned on the spectacles 58 worn by the user. When operative, the Delta wave motion sensor 64 detects the attitude of the user's head. As the user enters the Theta wave state, she may become drowsy and her head inevitably drops with the chin down. The motion sensor 64 mounted on the spectacles 58 she is wearing then detects this change in attitude and triggers, preferably, a tone generator to produce an audible tone. The tone alerts and awakes the user, causes her to raise her chin in attention, and forces her back into the Theta state thus preventing her from passing into the Delta wave sleep state. In effect, the present invention becomes a bio-feedback device.

The motion sensor 64 and tone generator are devices well known in the art. In an exemplary embodiment, the motion sensor 64 can be a simple mercury tilt switch that, when inclined at a certain angle, closes a circuit to activate the tone generator. Preferably, the motion sensor 64 is set up on the spectacles 58 so that when the user's head tilts forward beyond a 45 degree angle, the tone generator is set off.

As a modified bio-feedback device, the present invention can incorporate a circuit known in the art that increases the frequency of the signal output from the tone generator when triggered by the motion sensor. Accordingly, the flashing of the LEDs increases in frequency to keep the user's brain synchronized in the Theta wave state, which user might otherwise have drifted off into the Delta state. Similarly, the motion sensor can trigger an increase in the frequency of the audible tone, again forcing the user back into the Theta wave state.

The motion sensor and tone generator including the power source and speaker can be entirely self-contained, as shown in FIG. 5, or the devices may be separated. For instance, in another alternative embodiment, the tilt switch is used to send a control signal through the parallel port to flag the executing program that the user is close to passing into the Delta wave state. In response, a subroutine in the program can cause an alarm tone to be generated and sent to the headset. This accomplishes the same purpose as the separate tone generator mounted in the spectacles.

What is claimed is:

1. A brain wave synchronizer for stimulating the brain of a user to obtain a brain wave synchronization frequency, comprising:
   a personal computer including
      a medium containing an audio program and a brain wave synchronization program,
      a reader means for reading the audio program and the brain wave synchronization program,
      a controller means for receiving the audio program and brain wave synchronization program read by the reader means, a power source connected to the controller means,
      an interface port connected to the controller outputting from the personal computer a brain wave synchronization control signal and an audio control signal from the controller means in accordance with the brain wave synchronization program and the audio program;
   a light emitting device, connected to the interface port and actuated in accordance with the brain wave synchronization control signal, adapted to be disposed proximal to an eye of the user; and
   an audio emission device, connected to the interface port and actuated in accordance with the audio control signal, adapted to be disposed proximal to an ear of the user;
   whereby the light emitting device and the audio emission device stimulate the user's brain.

2. The brain wave synchronizer of claim 1, wherein the medium includes a magnetic memory in the personal computer.

3. The brain wave synchronizer of claim 1, wherein the interface port further comprises a parallel port.

4. The brain wave synchronizer of claim 1, wherein the light emitting device includes a light emitting diode mounted to an opaque lens of a spectacle frame adapted to be worn by the user, and the audio emission device includes an electromagnetic transducer.

5. The brain wave synchronizer of claim 4, wherein the synchronizer further comprises a motion sensor mounted on the spectacle frame, and a tone generator powered by the power source and connected to the motion sensor.

6. The brain wave synchronizer of claim 5, wherein the motion sensor includes a mercury switch.

7. The brain wave synchronizer of claim 6, wherein the opaque lens of the spectacle includes a peep hole.

8. The brain wave synchronizer of claim 7, wherein the audio emission device further comprises headphones.

9. The brain wave synchronizer of claim 4, wherein the spectacle further comprises a motion sensor connected to the controller, wherein the controller outputs a detect signal through the interface port to the audio emission device.

10. An arrangement, including earphones having first and second speakers and a stereo connector, for inducing brain waves with a predetermined synchronization frequency in the brain of a user, comprising:
    a recording medium with at least one, prerecorded control track, wherein the track includes a pulsed waveform signal having a frequency greater than a predetermined threshold flicker rate;
    a playback device being arranged to read the control track and to generate an electrical control signal corresponding to the control track;
    a visual presentation means for screening the eyes of the user from ambient light;
    a motion sensor disposed on the visual presentation means;
    a tone generator, electrically connected to the motion sensor, and providing a tone signal to the earphones;
    a connector means for connecting the visual presentation means electrically with the playback device;
    first and second lights, each mounted on the visual presentation means in front of a respective eye of the user;
    light-switching means for activating the first and second lights at the predetermined threshold flicker rate when the control signal has a substantially non-zero amplitude;
    sound-switching means for applying the control signal to the first and second speakers of the earphones and for producing audible tones; and
    a power source connected to the arrangement.

11. The arrangement according to claim 10, wherein the predetermined threshold flicker rate is approximately 40 Hertz.

12. The arrangement according to claim 11, wherein the recording medium includes a magnetic data medium.

13. The arrangement according to claim 11, wherein the first and second lights further comprise a light emitting diode.

14. The arrangement according to claim 11, wherein the motion sensor includes a tilt switch.

15. The arrangement according to claim 11, wherein the arrangement further comprises an unitary housing, and the recording medium and the playback device are contained in the unitary housing.

* * * * *